US006333300B1

(12) United States Patent
Bianchi et al.

(10) Patent No.: US 6,333,300 B1
(45) Date of Patent: Dec. 25, 2001

(54) WATER BASED DISPERSIONS OF PERCARBOXYLIC ACIDS

(75) Inventors: Ugo Piero Bianchi, Verona; Claudio Troglia, Milan, both of (IT)

(73) Assignee: Ausimont S.p.A., Milan (IT)

( * ) Notice: Subject to any disclaimer, the term of this patent is extended or adjusted under 35 U.S.C. 154(b) by 0 days.

(21) Appl. No.: 09/631,881

(22) Filed: Aug. 2, 2000

(30) Foreign Application Priority Data

Aug. 4, 1999 (IT) ................................. MI99A1757

(51) Int. Cl.$^7$ ................ C11D 7/22; C11D 7/32; C11D 7/38
(52) U.S. Cl. .............. 510/375; 510/303; 510/310; 510/313; 510/337; 510/476; 510/477; 510/479; 510/480
(58) Field of Search .................... 510/303, 310, 510/313, 337, 375, 476, 477, 479, 488

(56) References Cited

U.S. PATENT DOCUMENTS

| 4,992,194 | 2/1991 | Liberati et al. ................ 252/99 |
| 5,073,285 | 12/1991 | Liberati et al. ................ 252/94 |
| 5,246,612 | * 9/1993 | Van Dijk et al. ............... 252/102 |
| 5,633,223 | * 5/1997 | Vasudevan et al. ............. 510/303 |
| 5,817,614 | * 10/1998 | Miracle et al. ................ 510/376 |
| 5,952,279 | * 9/1999 | Fabry et al. .................. 510/276 |
| 6,096,098 | * 8/2000 | Miracle et al. ................. 8/111 |
| 6,117,357 | * 9/2000 | Kott et al. ................... 252/186.38 |

FOREIGN PATENT DOCUMENTS

| 0 325 289 B1 | 7/1989 | (EP) . |
| 0 763 595 A1 | 3/1997 | (EP) . |
| 0 852 259 A1 | 7/1998 | (EP) . |
| 0 890 635 A2 | 1/1999 | (EP) . |
| 1 010 751 A2 | 6/2000 | (EP) . |
| WO 00/27960 | 5/2000 | (WO) . |

* cited by examiner

Primary Examiner—Gregory Delcotto
(74) Attorney, Agent, or Firm—Arent, Fox, Kintner, Plotkin & Kahn, PLLC

(57) ABSTRACT

Water-based dispersions of the $\epsilon$-phthalimido peroxyhexanoic acid comprising as stabilizers copolymers of methyl-vinyl-ether with the acid and/or maleic anhydride, in 1:1 ratio with alternated structure, usable in detergent, hygienizing, cosmetic applications.

13 Claims, No Drawings

WATER BASED DISPERSIONS OF PERCARBOXYLIC ACIDS

The present invention relates to water dispersions of percaboxylic acids in crystalline form usable in detergent and/or hygienizing, cosmetic systems. More specifically water dispersions of crystals of $\epsilon$-phthalimido peroxyhexanoic acid, herein called PAP, having a high chemical stability and an improved physical stability, usable in detergent and hygienizing systems stable during the time for at least 6 months.

Organic peroxyacids are well known for their efficacy as bleaching and hygienizing agents also at low temperatures. To this class of compounds belong peroxycarboxylic acids solid at room temperature usable in formulations in powder or in tablets typical of the detergency.

Among peroxycarboxylic acids of particular interest the $\epsilon$-phthalimido peroxyhexanoic acid is very effective as bleaching, hygienizing and deodorizing agents, and in general as oxidizer, already under mild conditions of temperature and pH. The $\epsilon$-phthalimido peroxyhexanoic acid is suitable for the preparation of formulations for use in the detergent and cosmetic industry, since it has an exceptional thermal and at storage stability as well as a particularly favourable toxicological and ecotoxicological profile.

It is besides well known for the applications in the detergency and hygienizing field the use of liquid systems having an aqueous basis containing active principles not dangerous either for men or for the environment, having a sufficient chemical and physical stability such as to be used in consumer goods, for the distribution and exposure to the public for even long periods of time. For these systems an high chemical stability and an improved physical stability are required, in environmental temperature conditions from 15° to 35° C. for at least 6 months.

In the case of organic peroxyacids to be used as active principles for said liquid systems in the detergency and hygienizing field, it is difficult to formulate water-based systems with the above mentioned chemical physical stability properties.

In particular in the case of solid peroxyacids as the mentioned $\epsilon$-phthalimido peroxyhexanoic acid, the formulations having a water basis are heterogeneous systems, wherein the peracid crystals are dispersed in a continuous water phase.

It is known from the technology of the production of the $\epsilon$-phthalimido peroxyhexanoic acid to obtain dispersions of crystals of said acid in water mediums (slurry), characterized by a satisfactory chemical stability of the acid itself but by a low physical stability: in fact said slurries show, in absence of stirring, segregation and sedimentation also in short times. This means that these industrially useful products are difficult to be used as consumer goods due to their insufficient physical stability, since as knonw, for this application the products must be stable upon storage without stirring for at least 6 months.

It is known in the prior art the use of chemical auxiliary agents having properties of thickening and viscosity improver agents to be introduced in the water-based crystal dispersions to improve the physical stability thereof. But even though numerous auxiliary compounds are known, able to stabilize water-based dispersions of crystals of chemical compounds having relatively low reactivity, in the case of the $\epsilon$-phthalimido peroxyhexanoic acid, its high chemical reactivity makes it impossible to produce a water-based system having a high-chemical stability and improved physical stability lasting during the time.

The need was therefore felt to identify auxiliary agents suitable to develop water-based systems containing crystals of $\epsilon$-phthalimido peroxyhexanoic acid in the form of dispersions having a high chemical stability and improved physical stability during the time.

The Applicant has surprisingly and unexpectedly found auxiliary agents suitable for the preparation of chemically and physically stable water based dispersions of the $\epsilon$-phthalimido peroxyhexanoic acid.

An object of the present invention are water-based dispersions of the $\epsilon$-phthalimido peroxyhexanoic acid comprising as stabilizers copolymers of methyl-vinyl-ether with the acid and/or the maleic anhydride, in 1:1 ratio having an alternate structure.

Said polymers generally have a weight average molecular weight in the range 200,000–2,000,000.

Such stabilizers are in the market as, e.g., GANTREZ® by ISP.

The amount of PAP can range between 1–30% by weight, preferably between 3–20% by weight.

The amount of the stabilizers (auxiliary agents) of the invention generally varies in the range 0.2–5% by weight, preferably 1.5–4% by weight, still more preferably 2–4%.

The organic peroxyacid PAP is well known in the prior art for uses in the detergency and hygienizing field and also for its use in bleach, see EP 325,289 herein incorporated by reference.

The organic peroxyacid PAP contained in the suspensions (dispersions) of the present invention is under the form of crytalline particles having sizes generally in the range 5–200 micron, as determinable by optical microscope.

In the water-based dispersions of the $\epsilon$-phthalimido peroxyhexanoic acid of the present invention additional components such as polymers of natural origin of polysaccharide type, preferably selected from guar rubber and xanthan rubber, products described, for example in Merck Index, edition XII, number 4,602 of page 780 and number 10,191 of page 1,718, respectively, can optionally be present. In the suspension said optional stabilizers are in the range 0.1–1.5% by weight.

The total amount of stabilizers contained in the dispersion is in the range 0.2–5% by weight, preferably 1.5–4% by weight, still more preferably 2–4%.

Other optional components which can be added having the function to stop the catalytic action of heavy metal ions on the decomposition of the peroxyacid, are chelants and/or sequestrants in zounts from 0.005 to 5% by weight. Quinoline and its salts, alkaline metal polyphosphates, picolinic and dipicolinic acid, mono- or polyphosphonic acids, for example preferably the 1-hydroxyethylidene-1,1-diphosphonic acid (HEDP) can be mentioned.

The physical stability in the time, at room temperature, of the dispersions of the present invention (see for example Table 1) can be visually checked by ascertaining the unmixing presence or absence after six months. More suitably it can be checked that in the period of two months no unmixing appears and that the dispersion viscosity, generally in the range 500–2,000 centipoise, does not change in absolute value more than 10%, preferably 7%, when a copolymer of methylvinylether with maleic acid is used in 1:1 ratio having a weight average molecular weight 1,900,000. With said viscosity variations, the Applicant has found that the dispersion remains physically stable for at least six months.

The chemical stability during the time, at room temperature, of the dispersions of the present invention is determined by the active oxygen content, determined by iodometric titration and expressed in %, the 100% being defined the content of active oxygen at the beginning of the storage.

The viscosity of the PAP water-based dispersions according to the present invention, expressed in centipoise (cPs), is measured by Brookfield viscometer at 25° C. with rotary probe at 60 rpm.

The following examples are given for illustrative but not limitative purposes of the present invention.

EXAMPLE 1

25 g of alternated copolymer methylvinylether-maleic acid, having molecular weight $1.9 \times 10^6$, are slowly added to 385 g of distilled water. Stirring is maintained for 20 minutes until complete dissolution of the polymer.

170 g of ε-phthalimido peroxyhexanoic acid in powder are separately dispersed in 400 g of distilled water.

The two above described liquids are mixed together and kept under stirring for 20 minutes; a creamy liquid having a Brookfield viscosity of 830 cPs is obtained. The physical and chemical stability data during the time are reported respectively in Tables 1 and 2.

EXAMPLE 2

10 g of alternated copolymer methylvinylether-maleic acid, having molecular weight $1.9 \times 10^6$, are slowly added to 385 g of distilled water. Stirring is maintained for 20 minutes until complete dissolution of the polymer.

170 g of ε-phthalimido peroxyhexanoic acid in powder and 10 g of Guar rubber are separately dispersed in 400 g of distilled water.

The two above described liquids are mixed together and kept under stirring for 20 minutes; a creamy liquid having a Brookfield viscosity of 980 cPs is obtained. The physical and chemical stability data during the time are reported respectively in Tables 1 and 2.

EXAMPLE 3

10 g of alternated copolymer methylvinylether-maleic acid, having molecular weight $1.9 \times 10^6$, are slowly added to 385 g of distilled water. Stirring is maintained for 20 minutes until complete dissolution of the polymer.

170 g of ε-phthalimido peroxyhexanoic acid in powder and 3 g of Xanthan rubber are separately dispersed in 432 g of distilled water.

The two above described liquids are mixed together and kept under stirring for 20 minutes; a creamy liquid having a Brookfield viscosity of 910 cPs is obtained. The physical and chemical stability data during the time are reported respectively in Tables 1 and 2.

EXAMPLE 4 COMPARATIVE (COMP)

5 g of acrylic-sodiumacrylate-acrylamide acid copolymer, having molecular weight $5 \times 10^6$, commercialized as ECO-CLAR® by AUSIMONT, are solubilized in 825 g of distilled water.

A solution at pH 7, having a Brookfield viscosity of 960 cPs is obtained.

In such solution 170 g of ε-phthalimido peroxyhexanoic acid in powder are dispersed under mild stirring; a suspension having a Brookfield viscosity of 1,100 cPs is obtained. The physical and chemical stability data during the time are reported respectively in Tables 1 and 2. The chemical instability of the suspension is evident, wherefore the product has no interest from the application point of view.

EXAMPLE 5 COMPARATIVE (COMP)

170 g of ε-phthalimido peroxyhexanoic acid in powder are dispersed in 817 g of distilled water. 10 g of Guar rubber and 3 g of Xanthan rubber are added under stirring. The obtained mixture is subjected to stirring for 20 minutes until dissolution of the stabilizers; a suspension having a Brookfield viscosity of 1,100 cPs is obtained. The physical and chemical stability data during the time are reported respectively in Tables 1 and 2.

TABLE 1

| | physical stability in the time at room temperature | | |
|---|---|---|---|
| Examples | 48 hours | 8 weeks | 24 weeks |
| 1 | not unmixed viscosity 830 cPs | not unmixed viscosity 810 cPs | not unmixed viscosity 780 cPs |
| 2 | not unmixed viscosity 950 cPs | not unmixed viscosity 900 cPs | not unmixed viscosity 840 cPs |
| 3 | not unmixed viscosity 890 cPs | not unmixed viscosity 850 cPs | not unmixed viscosity 800 cPs |
| 4(comp) | not unmixed | — | — |
| 5(comp) | unmixed | — | — |

TABLE 2

| | chemical stability in the time at room temperature | | |
|---|---|---|---|
| Examples | 48 hours | 8 weeks | 24 weeks |
| 1 | 99.7% | 99.2% | 98.1 |
| 2 | 99.5% | 98.5% | 97.2% |
| 3 | 99.3% | 98.9% | 98.0% |
| 4(comp) | 71.0% | — | — |
| 5(comp) | 99.2% | — | — |

From the data reported in the Tables it can be noticed that physically stable water-based systems (Example 4 comp) containing in suspension fine crystals of the PAP peracid have not the necessary chemical stability, decreasing in quality due to the active principle decay, with loss of peroxidic oxygen.

Viceversa it happens that chemically stable water-based systems (Example 5 comp) containing in suspension fine crystals of the PAP peracid, have not the necessary physical stability, with loss of uniformity and decompostion in differentiated phases also just after the preparation.

What is claimed is:

1. Water-based dispersions of ε-phthalimido peroxyhexanoic acid comprising as stabilizers copolymers of methyl-vinyl-ether with maleic acid and/or maleic anhydride, in 1:1 ratio having an alternate structure wherein the amount of ε-hthalimido peroxyhexanoic acid ranges between 1–30% by weight and the weight average molecular weight of the stabilizer is in the range of 200,000 to 2,000,000.

2. Dispersions according to claim 1, wherein the stabilizer amount ranges from 0.2–5% by weight.

3. Dispersions according to claim 1, wherein at least one naturally occurring polymer is present as an additional component.

4. Dispersions according to claims 1, wherein components having the function to stop the catalytic action of heavy metal ions on the decomposition of the peroxyacid are present, in an amount from 0.005 to 5% by weight, selected from chelants and/or sequestrants.

5. Dispersions according to claim 4, wherein said components are selected from one or more of the following: quinoline and its salts, alkaline metal polyphosphates, picolinic and dipicolinic acid, mono- or poly phosphonic acids.

6. A method for stabilizing water based dispersions of ε-phthalimido peroxyhexanoic acid, said method comprising admixing copolymers of methyl-vinyl-ether and maleic acid and/or maleic anhydride, and water-based dispersions of ε-phthalimido peroxyhexanoic acid.

7. Dispersions according to claim 1, wherein the amount of ε-phthalimido peroxyhexanoic acid ranges between 3–20% by weight.

8. Dispersions according to claim 2, wherein the stabilizer amount ranges from 1.5–4% by weight.

9. Dispersions according to claim 3, wherein the stabilizer amount ranges from 2–4% by weight.

10. Dispersions according to claim 5, wherein said component is 1-hydroxyethylidene-1,1-diphosphonic acid (HEDP).

11. Dispersions according to claim 3, wherein the additional component is a polysaccharide.

12. Dispersions according to claim 11, wherein the polysaccharides are selected from guar rubber and xanthan rubber.

13. Dispersions according to claim 11, wherein the polysaccharides are in the range 0.1%–1.5% by weight.

* * * * *